United States Patent [19]

Dokkestul et al.

[11] Patent Number: 4,664,956

[45] Date of Patent: May 12, 1987

[54] METHOD FOR FOLIAGE AND OTHER PLANT MATERIAL PRESERVATION AND TOPICAL COLOR APPLICATION TO SAME

[76] Inventors: Jeffrey L. Dokkestul, 321 Goldstone Pl., Lake Mary, Fla. 32746; Leo A. Ochrymowycz, 237 W. Lowes Creek Rd., Eau Claire, Wis. 54701

[21] Appl. No.: 889,253

[22] Filed: Jul. 25, 1986

Related U.S. Application Data

[63] Continuation-in-part of Ser. No. 777,315, Sep. 18, 1985, abandoned.

[51] Int. Cl.$^4$ .......................... A01G 5/06; A01N 3/00; A41G 1/00
[52] U.S. Cl. .......................................... 428/22; 427/4; 427/354; 427/439
[58] Field of Search ........................ 427/4, 354, 439; 428/22

[56] References Cited

U.S. PATENT DOCUMENTS

| | | |
|---|---|---|
| 1,484,656 | 2/1924 | Koropp et al. |
| 2,026,873 | 1/1936 | Dux ............................................. 99/1 |
| 2,057,413 | 10/1936 | Bridgeman et al. .................... 47/58 |
| 2,083,191 | 6/1937 | Dux ................................................ 8/2 |
| 3,895,140 | 7/1975 | Sheldon et al. ...................... 428/22 |
| 4,278,715 | 7/1981 | Romero-Sierra et al. ............ 428/22 |
| 4,287,222 | 9/1981 | Robinson ................................ 427/4 |
| 4,328,256 | 5/1982 | Romero-Sierra et al. ............. 427/4 |

Primary Examiner—Michael R. Lusignan
Attorney, Agent, or Firm—Allen H. Erickson

[57] ABSTRACT

A method for preserving natural plant material comprising immersion, under about 3 to 30 psig (0.21–2.1 kg/cm$^2$ gauge) pressure, the material in ethylene glycol having a specific gravity of 1.03–1.10 for a period of 4 hours to 5 days. The material is then withdrawn, washed and dried for use or further treatment. The spent ethylene glycol is restored to its original volume with virgin ethylene glycol and re-used many times without purification. The preserved plant material is topically coated with a hydrophilic polymeric sealer optionally blended with a pigment.

35 Claims, No Drawings

METHOD FOR FOLIAGE AND OTHER PLANT MATERIAL PRESERVATION AND TOPICAL COLOR APPLICATION TO SAME

This application is a continuation-in-part of U.S. patent application Ser. No. 777,315, filed Sept. 18, 1985, now abandoned.

BACKGROUND

1. Field of the Invention

This invention relates to preservation of foliage or like materials derived from freshly harvested plants, either under cultivation or from indigenous wild sources, by pressure injection with a humectant. Such materials are intended for decorative utilization, to be offered for sale through the floral trades industry.

2. Information Disclosure Statement

The preservation and rendering natural in appearance of various plant materials for decorative, scientific, or display purposes of an aesthetic nature have been previously described in a variety of U.S. patents. Various parallel but unlike claims have been offered in other U.S. patents. Bridgeman et al. U.S. Pat. No. 2,057,413 describes a process for preserving living plants, cuttings, roots, bulbs and the like by coating with an aqueous emulsion of carnauba wax and an oleic acid salt.

In Dux U.S. Pat. No. 2,026,873, ruscus, already bleached and dyed, is softened by soaking 2-5 minutes in an emulsion of glycerin and sulphonated vegetable oil.

Dux U.S. Pat. No. 2,083,191 discloses a method for bleaching and/or deying foliage by submerging in ethyl or methyl alcohol at elevated pressure and temperature. The alcohol can be used only for 4-6 batches because water displaced from the foliage dilutes the alcohol to below 172 proof, too low for proper bleaching. This is true despite replenishment of alcohol absorbed by the foliage.

Korupp et al. U.S. Pat. No. 1,484,656 describes a process for producing decorative foliage. Cut plants are first dried, and then softened in an aqueous mixture of glycerin and formalin. After the plant surfaces are again dried, paint and/or varnish is applied to seal the glycerin within the treated plant. Complete pre-drying is essential to adhesion of the paint or varnish to the foliage.

In Romero-Sierra et al. U.S. Pat. Nos. 4,278,715 and 4,328,256, plant tissues are preserved with their natural color fixed by immersion in a complex solution containing (a) water, (b) an alcohol exchange medium, (c) preservatives and (d) buffers, mordants and modifiers.

Sheldon et al. U.S. Pat. No. 3,895,140 describes a process for preserving cut green foliage by extracting the normal fluids therefrom and imbibing a polyol, e.g. glycerin, in place thereof, at 140°-250° F. The preserved foliage may be dyed by soaking in pigment containing glycerin solutions.

It has been set forth in U.S. Pat. No. 4,287,222 to Robinson that fresh foliage material or other plant materials of a slightly dehydrated nature can be preserved by the injection under pressure of humectants belonging to the polyol class of materials, such as glycerin, ethylene glycol, and various polyethylene glycols. Most specifically, its claims demand that the density of such humectant material should fall within the specific gravity range of 1.10 and 1.16. Commensurate with such preservation techniques is the coloring of such materials by the direct combination of compatible dyes with the humectant agent, which are likewise forced under pressure into the plant materials. Subsequently, after appropriate duration of treatment with both humectant and dye, the plant material is withdrawn, rinsed in cold water, and dried to a natural state. It has been our experience, in fact, in evaluating the Robinson claims that no dye, out of fourteen classes of dyes involving at least one hundred combinations of dye materials, retained the desired stay-fastness in the plant foliage. In our tests, the specific dyes cited in the patent failed to achieve the desired result. Moreover, with the exception of the basic green-1 class of dyes, none of the dyes was uniformly absorbed into the material so as to render a natural color. No dye likewise was found which provided in the end result a stay-fastness of any significant duration. Finally, under no circumstances were we able to demonstrate consistency in preservation which resulted in the desired natural configuration, texture and structural retention of foliage with any combination of glycerol-water. At glycerol concentrations specified in the Robinson patent, and even at concetrations as low as those with a specific gravity of 1.08, extensive swelling and rupture of the plant tissue cells was observed by frozen section microscopic analysis. The glycerol humectant subsequently escaped the foliage structure by evaporation and biodegradation. The so-called preserved foliage rapidly curled, dried and decomposed.

SUMMARY OF THE INVENTION

In developing alternative methods, we have observed that numerous mitigating factors contribute to the behavior of natural plant material, including foliage, under humectant pressure treatment. These include the freshness and development stage of foliage, the type of foliage to be utilized and most critical for uniform large scale preparation of preserved materials, the nature of the humectant. Accordingly, a present objective of this invention is a method for treating freshly harvested plant materials, specifically foliage materials, which does not entail any prior process of denaturing such foliage materials by bleaching, the addition of chemical additives, or any process other than optional cleaning of the foliage by simple water-surfactant wash prior to its preservation. Even such washing may be omitted if the foliage is free of any surface contaminants. The objective is to yield as an end result a material that has long term shelf life and long term use for decorative or ornamental purposes, as well as eductional, expositional, and sentimental purposes. More specifically, an objective is to produce a treated and coated materials which has a minimum shelf life of 6 months at 60°-90° F. (16°-32° C.) and 50 percent relative humidity. More preferably, a shelf life of at least 1 year is desired. Because the prime harvest season is relatively short, foliage is generally treated for preservation and stored for later color application. Thus, the treated but unsealed and/or uncolored material will preferably have a shelf life of at least 4 months. However, the scope of the method does not require that the terminal appearance of the foliage is to be absolutely natural and lifelike, although the process described within will in fact meet such qualifications. It is possible by the present invention to generate foliage having virtually any color, whether natural or exotic in nature, dependent only on availability of the requisite colored coating formulation. Thus, foliage of numerous colors, as well as foliage having a colorless appearance, can be formulated and prepared to have the configuration of living foliage. The terminal objective of the present invention is to in fact provide a process at a high level of performance conducive to large scale manufacturing production of said materials. Whereas the mere preservation of the foliage material may not involve a specific dexterity related to artistic considerations, the coloration of the material by application of surface coatings and its texturing to natural color does involve the aesthetic judgement of artisitic color texturing. However, the materials involved in application of such artistic texturing are formulations of commercially available materials designed to achieve specific aesthetic effects.

In summary, this invention is a method for preserving natural plant materials, including cut foliage, to enhance their appearance and decorative use.

A batch of the plant materials is first immersed in a starting volume of ethylene glycol having a specific gravity of 1.03 to 1.10 at a pressure of about 3–30 psig (about 0.21–2.1 kg/cm$^2$ gauge) for a period of 4 hours to 5 days. This range of specific gravity corresponds approximately to 23–77 percent ethylene glycol. The plant fluids are partially exchanged with ethylene glycol, producing treated plant materials containing ethylene glycol of specific gravity 1.025–1.10. The lower value of specific gravity, i.e. 1.025, corresponds to approximately 19 percent ethylene glycol.

The treated materials are withdrawn from the pressurized immersion in the spent ethylene glycol and washed to remove excess ethylene glycol from their surface. The materials are then dried to the touch for use or further treatment.

The spent ethylene glycol is restored to its starting volume by adding ethylene glycol having a concentration no lower than specific gravity 1.03. Preferably, virgin ethylene glycol is used. The restored humectant is re-used to treat additional batches of plant materials according to this process.

The use of fungicides, bactericides, dyes, buffers, mordants and/or modifiers in the exchange medium is avoided.

Following treatment with ethylene glycol, the plant materials may be topically coated by one of several methods.

In one method, the materials are first dipped in a hydrophilic polymeric subcoating sealer. The sealed materials may then be topically tinted, if desired, by dip-coating or spraying with a blend of pigment in a water dispersible adhesive or polymeric medium.

Alternatively, the foliage materials may be sealed and tinted in a single step, for example with a blend of hydrophilic polymer and pigment.

DESCRIPTION OF THE PREFERRED EMBODIMENTS

1. Preservation and Permanency Retention of Foliage Structure

This invention comprises a method which demands as an essential consideration the utilization of ethylene glycol in the specific gravity range from 1.10 to as low as 1.03. No other humectant composition has been found to be suitable to meet the same quality of product as that to be obtained from ethylene glycol. The best results are obtained in a specific gravity range of 1.05–1.10, but operational product can be obtained for material of a specific gravity down to as low as 1.03. Optimum results, however, are obtained for the above specific gravity range of 1.05 to 1.10, as measured at 20°

C. The exemplary preservation then involves the bundling of freshly cut foliage which has not been precoated in any way by any agent. Most specifically, prohibition is demanded against the utilization of any other chemical agents, such as fungicides or interim preservatives often utilized to coat foliage. Such materials should all be excluded from material to be utilized for preservation. It is often advantageous to remove any surface contamination of foreign matter, e.g. dust or dirt adhering to said foliage by a brief washing with cold water, with or without detergent. At the same time, however, certain foliages which have been desiccated to a considerable degree may likewise be preserved, as long as their structural integrity was retained following desiccation. Thus, up to about three pounds of all such foliage per gallon of ethylene glycol (0.36 kg per liter ethylene glycol) are inserted into a large immersion pressure vessel and ethylene glycol is subsequently added to the same vessel. Alternatively, the humectant is placed in the vessel first.

To the ethylene glycol may be added an antifoaming agent in order to suppress foaming or gas entrainment during the pumping of ethylene glycol preservative-humectant in a continuous operation process. Antifoam agents having a silicone base are preferred, although other types may also be satisfactory. The antifoam agent of choice is a silicone defoamer manufactured by Dow-Corning Company of Midland, Mich. The specific serial grade and product line is Anti-Foam DB-1100A. For two hundred gallons (750 liters) of ethylene glycol, approximately three ounces (85 grams) of the foaming agent is added. This need not be recharged except after extensive reutilization of the ethylene glycol so as to preserve foam suppression. In one embodiment, the immersion vessel containing ethylene glycol and fresh foliage is then sealed and external pressure of air or other inert gas is applied.

While this method is satisfactory for some materials, most foliage species are more uniformly treated in a shorter time period by expressly eliminating gas from the pressure tank. In the absence of vigorous agitation, gas bubbles adhere to foliage surfaces and prevent penetration of humectant into the foliage.

Therefore, in the preferred embodiment, the humectants are introduced with a strong flow from the bottom of the vessel to wash out all traces of gases clinging to the foliage surfaces and the gases entrained in the humectant. As the liquid flow is continued and essentially all gas bubbles are purged from the pressure vessel, the outflow at the top of the vessel is closed and hydrostatic pumping of humectant is continued until the desired internal pressure is achieved. Other methods of pressurizing the vessel may alternatively be used, provided no gas is introduced into the vessel, and the foliage is treated in humectant essentially free of gases. We have observed that for many species, elimination of gas bubbles enables the production of a high quality, uniformly preserved material in a much shorter time. For most product lines, good penetration and preservation with ethylene glycol is thus achieved in treatment periods as short as 4 hours. More woody foliage and foliage having a dense structure or massive texture may require longer periods of pressure soaking (eight to twelve hours being typical).

In addition, the elimination of entrained gas by this method also reduces the effects of foliage maturity and post-harvest age upon the required treatment time. Thus, a uniform, relatively brief treatment period may be used to treat a wide variety of materials without regard to such factors as maturity or post-harvest age.

From a commercial standpoint, it is advantageous to minimize the processing time without sacrificing quality. We have found that, depending on the particular plant material and operating temperature, an immersion pressure of 3-30 psig (0.21-2.1 kg/cm$^2$ gauge pressure) produces the best results in a short processing time and at the lowest cost.

The rate of absorption of the humectant and curing of the foliage is directly proportional to freshness of foliage, temperature of ethylene glycol, and incrementally related to pressure. The specific pressure range is not critical per se. A minimum, however, of approximately 3 psig (0.21 kg/cm$^2$ gauge) to a maximum of approximately 30 psig (2.1 kg/cm$^2$ gauge) produces satisfactory results. In fact, the preservation and the humectant absorption of the foliage may be done entirely without pressure, but requires considerably longer duration for absorption of the humectant. The optimum temperature range is from 70° F. (21° C.) to approximately 105° F. (41° C.), and the best results are achieved with the freshest foliage. Light leaf foliages are readily preserved under such treatment for a period of 4-48 hours. Heavier wooded foliages, such as leather leaf fern, require a minimum of 48 hours of such pressure treatment. Heavy wooded foliages, leather leaf fern being a good example, and other examples such as heather or palms of various kinds, may in fact be improved in quality of natural characteristic by subsequently withdrawing from the pressure treatment process and soaking for an additional period of up to one week at atmospheric pressure in ethylene glycol of specific gravity 1.05 or higher. Preferably, ethylene glycol of specific gravity between 1.07 and 1.10 is used. During the pressure treatment, and during atmospheric soaking, the bulk materials are preferably periodically or continuously agitated in order to expel any adhering or entrained air-gas bubbles from the foliage matrix. This may be done, for example, by tipping, turning or rolling the immersion tank to achieve liquid movement through the foliage.

It is most convenient to withdraw the ethylene glycol in large quantity from the pressure tank by an efficient surge pump. The antifoam agent will suppress all foaming during transfer. Likewise, loading of such tanks is best achieved with a high volume surge pump. During such pressure treatment with ethylene glycol, most of the green coloration of chlorophyll is lost from the foliage structure and the foliage assumes an off-gray to a grayish-tan coloration.

Freshly withdrawn foliage is stacked in piles on racks from which excess ethylene glycol is drained into a catch tank. Subsequently, the foliage is washed with cold water to which has been added only a very small amount of a non-ionic detergent of any variety, or a blended surfactant such as castile soap, e.g. Lux TM soap. One surface adhesion of ethylene glycol has been removed, the foliage is shaken free of excess wetting due to water and hung to air dry to a state equivalent to that of natural non-wetted foliage. The required time for drying is inversely proportional to the velocity of air movement within the racked foliage. The drying time may be reduced by increasing air circulation through the hung foliage and/or by a slight elevation of temperature. Heavily structured foliage, such as leather leaf fern or various palms, may on occasion require a second washing due to a depressurizing bleed-out of the humectant ethylene glycol from the material. Subsequent topical coloration of the preserved foliage demands that the bulk of ethylene glycol be cleaned from the foliage surface. Therefore, the number of washings required to bring the foliage to a surface clean condition varies. Excessive surface ethylene glycol is readily apparent by appearance and feel. Strictly speaking, the dried foliage surface is not free of ethylene glycol. In all cases, a very thin layer of humectant remains at the foliage surface because of capillary action.

Despite dilution with plant moisture, the ethylene glycol recovered from the preservation process may be reutilized in effect indefinitely witout any apparent degradation. The only requirement is that additional ethylene glycol having a specific gravity no lower than 1.03 must be added back to the used ethylene glycol to bring the total volume back to the starting quantities. Preferably, virgin ethylene glycol is used. We have observed reutilization of a crude batch of ethylene glycol by the incremental readdition of virgin ethylene glycol for over eighty consecutive preservation runs without loss in product quality. Thus, purification of the ethylene glycol, e.g. by distillation, is rarely if ever required. Depending on foliage, anywhere from five to fifteen percent of the original ethylene glycol is taken up from a batch-volume ratio of three pounds foliage per gallon (0.36 kg per liter). During such reuse of the ethylene glycol, its specific gravity rapidly falls from the initial starting value of 1.10 to incremental values significantly below 1.10 for example, to 1.07 or 1.05, or even 1.03.

For some foliage lines it is often advantageous to allow the material to cure for one week to two weeks prior to its subsequent utilization. However, light grained foliage such as sprengeri or plumosus dry quickly and leave very little residual humectant and may be carried on to the coloration step almost immediately.

In the event that foliage need not be colored for its end use, it may be utilized in its preserved form in a tannish-gray appearance It slowly changes over a period of four to five days from a tan gray to an amber brown color. If exposed to sunlight for varying durations, e.g, 20-100 hours the coloration bleaches to a pale buckskin tan. It is the intent of this invention to market such tan colored foliage under the color label of "Buckskin." Most foliages so exposed to sunlight achieve the "Buckskin" coloration within a period of four to five days for an eight hour day of direct sunlight exposure.

The plant material which may be processed by the above invention is most extensive and includes, but is not specifically limited to the following. However, for commercial purposes, the following bear specific note: sprengeri, plumosus, tree fern, ming, plumosus stringers, marsh grass and pepper grass are preserved in two days preservation time. Deer foot moss, Spanish moss, reindeer moss, and other such mosses are preserved in one day preservation time. Various ferns, including leather leaf fern, sword fern, Florida flat fern, and all other such ferns, are preserved in two to three days, followed by optimal results obtained from an additional weak of soaking in ethylene glycol at atmospheric pressure. Magnolia and Palmetto likewise require the same treatment as leather leaf fern. Sparkle berry, aspidistra, Florida huckleberry, and any other variety of huckleberries; ivies of all types, including large ivy, grape ivy, small ivy, and ivies related to the mistletoe varieties, can be treated in three days without additional soaking at atmospheric pressure. Florida ruscus, coon tie fern, West Coast huckleberry, West Coast Salal, bear grass, tipi fern, champas, cypress, small Florida bamboo, medium bamboo and large bamboo require three days preservation time without additional soaking. All varieites of pines, spruces and firs, including Frasier fir, Austrian pine, Florida shortleaf pine, white pine, black spruce, Hamilton spruce, 2 hemlocks, and all other evergreens, require three days of treatment. The preceding is but a partial list of plant materials which have been processed successfully through the utilization of the present invention. Other foliages are amenable to the same process as described or with only minor variations. The treatment time may vary, depending on the production schedule and plant foliage quality.

2. Application of Lifelike Natural Green Colorant and Other Colorants

The desirable color and hue may be applied to the preserved plant material by topical-dip application of an acrylic base subcoating, followed by a tinting applied under pressure spraying. Alternatively, a one-step topical coating may be applied, saving time and expense. A wide variety of colors and hues may be applied without restriction to the nature of foliage. The critical factor in the 2-step process is that an appropriate underlayment is first applied to the foliage followed by a very light tinting to bring the foliage to the desired hue. In the case of green or natural appearance the formulation is subsequently described. For purposes of example, alternate colorations will likewise be described. The practice in general follows in such fashion: The plant material, such as a single leaf or multiple bunches of sprigs, having previously been washed of all suface humectant, is air dryed, generally above 70° F. (21° C.), to the touch. This material is dipped into a hydrophilic base coating which totally masks any underlaying color of the foliage and adheres to the foliage surface despite the layer of ethylene glycol. During the preservation process the natural chlorophyll green color of the foliage has been destroyed due to dehydration, chemical degradation, or photo fading. Once the base coating has been dip applied and dried, the primary color tonent is applied under pressure spray. The critical feature to be achieved is a coating of high integrity, high retentiveness, no tackiness, and luster or texture comparable to natural foliage. If alternate shades, colors, and hues are required, these may be achieved without intent to duplicate or simulate natural appearance.

The following is an exemplary formulation for a natural chartreuse green foliage blend. The first to be described is the base coating which is applied by dip to the foliage material. This does not exclude numerous other possible combinations which may result in satisfactory product quality. The base coating achieves its filming and sealing properties from an acrylic-glue blend underlayment. The acrylic underlayment utilized within the exemplary process is manufactured by McWorter Chemical Corporation, Carpentersville, Ill., and marketed under the trade name of Aquo-Mac TM 607 or 609 series. Likewise, the exemplary pigments utilized for the application of appropriate colorants are marketed by Val-Spar Manufacturing, Rockville, Ill., and marketed under the Tint-EZE TM label. Desired green color combinations are obtained from the four component listing of constituents. These include: Pthalogreen-623, Organic Yellow-611, Titanium White-600, and Lamp Black-691. In the subsequent tinting process the base media can be any variety of water dispersable adhesive or polymeric media which binds well to the acrylic underlayment and like the base coat imparts sealant properties upon the foliage. In our process optimal results have been obtained with one of two alternative materials. These include a formaldehyde based adhesive manufactured by H. B. Fuller Company of Minneapolis, Minn., Adhesive X-3801; or alternatively, an antitranspirant manufactured by Agro-K Corporation of Minneapolis, Minn., marketed under the label of Envy-Antitranspirant TM. The preparation of stock solutions of base colorants and tinting agent involve the following:

A. Base Coating Colorant Combination—Green.

Four cups (0.95 liter) of the Pthalogreen-623, two cups (0.47 liter) of Organic Yellow-611, and one cup (0.24 liter) of Titanium White-600, are blended with seven cups (1.656 liter) of water to form a dispersed paste. To this dispersed paste is mixed two gallons (7.57 liters) of the Aquo-Mac TM 607 or 609.

B. Stock Solution Base Colorant—Yellow.

Five cups (1.18 liters) of Organic Yellow-611 is likewise blended with five cups (1.18 liters) of water to produce a dispersant-paste. This is likewise blended with two gallons (7.57 liters) of Aquo-Mac TM 607 or 609. Using the above stock blends, the mixture designed as the dipping coat is then formulated as follows: Seven quarts (1.656 liters) of the green pigment stock, A, are mixed with six quarts (1.42 liters) of the yellow pigment stock, B, and added to two gallons (7.57 liters) of 50:50 aqueous Adhesive 3081, or two gallons (7.57 liters) of 50:50 aqueous Envy-Antitranspirant TM. After efficient blending the total mixture is then diluted with twenty gallons (75.7 liters) of methyl alcohol. This then constitutes the base dip material. In the event that foliage is being utilized which is very nonuniform in color due to the preservation process, or due to bleach out of background colorants due to the preservation process or sun exposure, trace amounts of Lamp Black-691 are then blended to obtain depth of tone. On most occasions, no Lamp Black need be added. The amounts which are added in exceptional cases constitute quantities in the vicinity of a tablespoon (15 mL) or less. If a heavier application of coating in the base coating dip process is desired, then lesser quantities of methanol are utilized. Likewise, lighter coverage may be obtained by using a higher dilution of methanol.

The pigment toning material which is applied as a spray blend to the base coated foliage is prepared by utilizing one part of yellow pigment blend B to four parts of pure methanol. To diminish the intensity of the yellow and to render it more of a chartreuse green color, small amounts of the green pigment base A are subsequently added. Thus a typical formulation would involve one gallon (3.78 liter) of pigment B, four gallons (15.14 liters) methanol, and one-half cup (0.12 liter) of pigment blend A.

The actual application of colorant to foliage is a simple direct process. The foliage as individual sprigs or as loosely tied bundles is dipped into the base coat blend and swished through this media. Entrained or adhering air bubbles are so purged from the foliage surface. The foliage is then shaken to drain any excessive film of the colorant base coat blend and immediately hung to dry in an inverted or upright configuration which allows good passage of air provided by natural air movement or enhanced by fan circulation. At 70° F. (21° C.) and 50% relative humidity, the base coat dries on most foliages to a state of low-tackiness within five to ten minutes. An additional one-half hour of curing is recommended prior to subsequent toning. Toning, however, may be delayed indefinitely.

In this example, the natural tone blend of yellow is applied by one of two methods utilizing a commercial spray painting mechanism, but may be obtained with any nature of air-assisted, air brush, film application spray gun. Thus, utilizing the blend of toner containing pigment B, methanol, and small amounts of pigment A, a Binks-Vantage TM BB-2 Gun fitted with a nozzle size of 0.015 inch (0.38 mm) is fed through a paint pot reservoir of 15–35 psig (1.05–2.45 kg/cm$^2$ gauge) within a well ventilated spark-free paint booth. Individual bunches of foliage are toned to aesthetic standards depending upon individual bunch size and foliage type over two to ten second durations. Individual operators develop varying proficiencies of application of toner. The Binks series mechanisms involve a fixed paint application spray cone and operate at variable air assisted pressure. Alternatively, utilizing the same toner blend, an air-over-fluid standard paint gun with paint feed from pressure pot will prove functional. Any spray gun possessing variable flow and variable pattern parameters, and preferably having an external paint mix mechanism, provides satisfactory results.

Immediately after spraying, the toned foliage bundles are laid on flat racks, or they can be directly hung. Within seconds after application the toner has dried to insignificant tackiness so that individual bundles of foliage or individual sprigs of foliage do not adhere to each other or disrupt the finish by contact. However, at 70° F. (21° C.) an additional thirty minutes of drying time on such flat racks is allowed prior to packaging. Alternatively, the toned foliage bundles or individual springs may be attached to a mobile conveyor in a heated, 110° F. (43° C.), air drying tunnel and within less than three minutes the material exits the tunnel, ready for packaging. Individual bundles are bagged in polypropylene clear bags according to shipment scale design and twist-tie sealed.

As described in the above example, the coating so applied renders the foliage natural and lifelike in color and inhibits transpiration of entrained humectants. Its shelf like under the conditions of production are significantly improved due to the application of the base coating and its sealant components of adhesive or antitranspirant such as outlined above. Numerous other possible combinations of antitranspirants or sealing adhesives are feasible for this process.

Foliage which is to be rendered bleached of color due to sun bleaching after preservation in ethylene glycol is likewise dipped with a sealant. The preferred sealant blend is a combination involving the Fuller Adhesive X-3801 or Agro-K Corporation Envy-Antitranspirant TM blended with twice the volume of Aquo-Mac TM 607 or 609 Acrylic Media and subsequently diluted with an equal volume of water. This in turn is then diluted with ten parts by volume of methanol. The total milky dispersant blend is utilized as a dip on the buckskin line of foliage and allowed to air dry in identical fashion to the pigment application base coat. No additional colorant need be added. However, if pure white foliage is to be produced, such a transparent base coat is subsequently oversprayed with any variety of Titanium White-600 tone coatings by spray application. A typical tone coating by spray applications would involve a blend of one cup (0.24 liter) of Titanium White-600 dispersed in one cup (0.24 liter) of water which in turn is added to one gallon (3.78 liter) of Aquo-Mac and one-half gallon (1.89 liter) of Antitranspirant or Adhesive 3801 and diluted with ten gallons (37.8 liters) of methanol. White toning is applied in similar fashion to that described for the application of the natural chartreuse green toning color.

The above are simple examples; numerous other possible color combinations may be applied using various varieties and classes of pigments. Thus, for example, foliage may be produced of a red, pink, yellow, blue, gold, silver, orange or any other natural or unnatural blend of colors.

Although the two-step process of sealing and tinting described thus far works well with all types of foliage materials, most foliage types may be effectively sealed and tinted in a single step with a hydrophilic blend of polymer and pigment. Other possible components may include extenders, dispersants, thickeners, solvents, antifoam agents and pH control agents. This topical coating is most easily applied as a dip-coat, but it may also be applied by spraying. The hydrophilic nature of the blend is most critical to ensure adhesion to the effectively wet foliage surface having ethylene glycol adhering to it.

The following exemplary one-step Formulation A renders preserved foliage natural in color and general appearance, and uses a green pigment latex which provides uniform coverage and a depth of tone which masks all decolorization effects resulting from the preservation process. The polymer latex vehicle is used to disperse and overlay the foliage in a film. For this purpose, we have found that vinyl acetate/hydroxyethyl acrylate copolymers having an average range of molecular weights of 30,000 to greater than 35,000 are the preferred filming agents.

| Formulation A for Latex Green Base Coat | | |
|---|---|---|
| Ingredient | Range Percent by Weight | Function |
| Chrome Green (Cr$_2$O$_3$) | 10.0–30.0 | Pigment |
| Water Ground Mica | 1.50–5.00 | Extender |
| Sodium Polyphosphate | 0.50–1.00 | Dispersant |
| Sodium Carboxymethyl Cellulose | 0.30–0.70 | Thickener |
| Methocel TM Antifoam | 0.02–0.10 | Antifoam |
| Ammonia (0.88 H$_2$O solution) | 0.01–0.07 | Alkalinity control |
| Butylacetate | 2–3 | Coalescing solvent |
| Vinylacetate/Hydroxyethyl Acrylate/Acrylic Acid 45:45:10 Copolymer (50% solids in H$_2$O dispersion) | 30.0–45.0 | Film former |
| Water | 30.0–45.0 | |
| | 100.00 | |

This formulation effectively masks the unnatural faded greyish-green appearance of the foliage resulting from preservation with humectant ethylene glycol. The chrome green pigment pleasingly matches the natural color of many foliages. Other pigments are used to achieve whatever tint is desired.

Additional artistic effects may be obtained by further steps of spraying or dip-coating.

Another example of an effective hydrophilic one-step blend is shown as Formulation B, which is in the form of a water latex dispersed emulsion. The formulation is colorless without added pigment. Pigment is added to the formulation to obtain coloration, and is selected to achieve the desired aesthetic effect in the final coated foliage materials.

| Formulation B for Latex Emulsion Base Coat-Colorless for Pigment Blends | | |
|---|---|---|
| Ingredient | Range Percent by Weight | Function |
| Pigment - inert and variable in blends (not part of wt %) | | |
| Talc or Water ground mica | 7.0–15.0 | Extender |
| Tamol TM 731 (Rohm and Hass) | 1.50–2.50 | Surfactant |
| Methocel TM Antifoam | 0.10–0.30 | Antifoam |
| Hydroxyethyl Cellulose | 0.20–0.50 | Thickener |
| Butylacetate | 1.00–3.00 | Coalescing Solvent |
| Ammonia (0.88 $H_2O$ Solution) | 0.02–0.07 | Alkalinity Control |
| Vinylacetate/Vinyl "Versatate" TM 55:45 Copolymer (52% solids in $H_2O$ dispersion) | 40.0–60.0 | Film Former |
| Water | 25.0–40.0 | |
| | 100.00 | |

The indicated percentage component ranges are exemplary only, and are not intended to be limiting. Furthermore, all of the listed components in Formulation A and B need not be used in a particular blend. For example, an alkalinity control agent is not always necessary.

Following the application of Formulations A or b or similar blends, foliage may be enhanced in aesthetic effect by further steps of spraying or dip-coating with a wide variety of colored or clear coating materials.

Plant materials treated according to the present invention retain the flexibility of their freshly cut state. The strength is retained or enhanced, resulting in a long shelf life and a long useful life for decorative, scientific or display purposes. Furthermore, dust and grime adhering to the plant materials as a result of storage or exposition may be easily removed by washing with cool or cold water, optionally containing a weak non-ionic detergent or castile soap, to restore the materials to a clean, aesthetically attractive state.

Having described our invention we claim and desire to obtain by Letters patent the following:

1. A method for preserving natural plant materials, including cut foliage, comprising the steps of:
   (a) immersing a batch of said plant materials in a starting volume of ethylene glycol having a specific gravity of 1.03 to 1.10 at a pressure of about 3 to about 30 psig (0.21 to 2.1 kg/cm$^2$ gauge) for a period of 4 hours to 5 days to effect exchange of plant fluids in said plant materials with said ethylene glycol and produce treated plant materials;
   (b) withdrawing said treated plant materials from the pressurized immersion in the spent ethylene glycol;
   (c) washing excess ethylene glycol from the surface of said treated plant materials;
   (d) drying said treated and washed plant materials;
   (e) adding ethylene glycol having specific gravity no lower than 1.03 to said spent ethylene glycol from step (b) to restore the starting volume; and
   (f) preserving a further batch of said plant materials in said restored starting volume of ethylene glycol in accordance with steps (a)–(e).

2. The method according to claim 1, wherein said immersed batch of plant materials is periodically or continuously agitated to expel gas bubbles therefrom.

3. The method according to claim 1, comprising the further step of immersing said treated plant materials in ethylene glycol having a specific gravity of 1.05–1.10, for up to 1 week at atmospheric pressure, before washing step (c).

4. The method according to claim 1, comprising the further step of exposing said washed and dried plant material to sunlight for 20 to 100 hours to produce material having a pale buckskin tan coloration.

5. The method according to claim 4, comprising the further step of coating said washed and dried plant material with a sealant prior to or following sunlight exposure.

6. The method according to claim 1, comprising the further step of sealing said dried plant materials from step (d) to prevent bleed-out of ethylene glycol and enhance the shelf life and utility of said plant materials.

7. The method according to claim 6, wherein said sealing comprises dipping said dried plant materials into a blend of an acrylic base, water and a water dispersible adhesive or polymeric antitranspirant.

8. The method according to claim 1, comprising the further steps of dipping said dried plant materials from step (d) into an acrylic base and glue subcoating to seal and to mask the color of said materials, removing and drying said subcoated materials, and spray painting with one or more color pigments blended with a water dispersible adhesive or polymeric medium to tint said materials.

9. Natural plant materials treated according to the process of claim 8, wherein said materials contain ethylene glycol of specific gravity 1.025 to 1.10, sealed within said materials by an acrylic base and glue subcoating, and are spray painted with one or more pigments blended with a water dispersible adhesive or polymeric medium.

10. The method according to claim 1, comprising the further step of topically coating said dried plant materials from step (d) with a tinting sealer comprising a hydrophilic blend of polymer and pigment.

11. The method according to claim 10, wherein said polymer comprises a vinyl acetate/hydroxyethyl arcylate copolymer.

12. Natural plant materials treated according to the process of claim 10, wherein said materials contain ethylene glycol of specific gravity 1.025 to 1.10 sealed within said materials by a tinting sealer comprising a hydrophilic blend of polymer and pigment.

13. A method for preserving natural plant materials, including cut foliage, comprising the steps of:
   (a) immersing a batch of said plant materials in a starting volume of ethylene glycol having a specific gravity of 1.05 to 1.10 at a pressure of about 3 to about 30 psig (0.21 to 2.1 kg/cm$^2$ gauge) for a period of 1 to 5 days to effect exchange of plant fluids in said plant materials with said ethylene glycol and produce treated plant materials;
   (b) withdrawing said treated plant materials from the pressurized immersion in the spent ethylene glycol;
   (c) washing excess ethylene glycol from the surface of said treated plant materials;
   (d) drying said treated and washed plant materials;
   (e) adding virgin ethylene glycol to said spent ethylene glycol from step (b) to restore the starting volume; and (f) preserving a further batch of said plant materials in said restored starting volume of ethylene glycol in accordance with steps (a)–(e).

14. The method according to claim 13, comprising the further step of immersing said treated plant materials in ethylene glycol having a specific gravity of 1.05–1.10, for up to 1 week at atmospheric pressure, before washing step (c).

15. The method according to claim 13, comprising the further step of exposing said washed and dried plant material to sunlight for 20 to 100 hours to produce material having a pale buckskin tan coloration.

16. The method according to claim 15, comprising the further step of coating said washed and dried plant material with a sealant prior to or following sunlight exposure.

17. The method according to claim 13, comprising the further step of sealing said dried plant materials from step (d) to prevent bleed-out of ethylene glycol and enhance the shelf life and utility of said plant materials.

18. The method according to claim 17, wherein said sealing comprises dipping said dried plant materials into a blend of an acrylic base, water and a water dispersible adhesive or polymeric antitranspirant.

19. The method according to claim 13, comprising the further steps of dipping said dried plant materials from step (d) into an acrylic base and glue subcoating to seal and to mask the color of said materials, removing and drying said subcoated materials, and spray painting with one or more color pigments blended with a water dispersible adhesive or polymeric medium to tint said materials.

20. Natural plant materials treated according to the process of claim 19, wherein said materials contain ethylene glycol of specific gravity 1.05 to 1.10, sealed within said materials by an acrylic base and glue subcoating, and are spray painted with one or more pigments blended with a water dispersible adhesive or polymeric medium.

21. The method according to claim 13, comprising the further step of topically coating said dried plant materials from step (d) with a tinting sealer comprising a hydrophilic blend of polymer and pigment, to seal and color said plant materials in a single topical application.

22. A method for preserving natural plant materials, including cut foliage, comprising the steps of:
(a) placing a batch of said plant materials in a pressure vessel;
(b) introducing ethylene glycol having a specific gravity of 1.03 to 1.10 from the bottom of said pressure vessel with a strong flow to remove gases clinging to said plant materials and gases entrained in said ethylene glycol, until said pressure vessel is filled with said plant materials immersed in ethylene glycol essentially free of gases;
(c) sealing said pressure vessel and pressurizing to an internal pressure of about 3 to about 30 psig (0.21 to 2.1 kg/cm$^2$ gauge) without introducing gases into said vessel;
(d) maintaining said plant materials at said pressure for 4 hours to 5 days to effect exchange of plant fluids in said plant materials with said ethylene glycol and produce treated plant materials;
(e) withdrawing said treated plant materials from the pressurized immersion in the spent ethylene glycol;
(f) washing excess ethylene glycol from the surface of said treated plant materials;
(g) drying said treated and washed plant materials;
(h) adding ethylene glycol having a specific gravity no lower than 1.03 to said spent ethylene glycol from step (e) to restore the starting volume; and
(i) preserving a further batch of said plant materials in said restored starting volume of ethylene glycol in accordance with steps (a)–(h).

23. The method according to claim 22, comprising the further step of adding an antifoaming agent to said starting volume of ethylene glycol.

24. The method according to claim 23, wherein said antifoaming agent has a silicone base.

25. The method according to claim 22, wherein said immersed batch of plant materials is periodically or continuously agitated to expel gas bubbles therefrom.

26. The method according to claim 22, comprising the further step of immersing said treated plant materials in ethylene glycol having a specific gravity of 1.05–1.10, for up to 1 week at atmospheric pressure, before washing step (f).

27. The method according to claim 22, comprising the further step of exposing said washed and dried plant material to sunlight for 20 to 100 hours to produce material having a pale buckskin tan coloration.

28. The method according to claim 27, comprising the further step of coating said washed and dried plant material with a sealant prior to or following sunlight exposure.

29. The method according to claim 22, comprising the further step of sealing said dried plant materials from step (g) to prevent bleed-out of ethylene glycol and enhance the shelf life and utility of said plant materials.

30. The method according to claim 29, wherein said sealing comprises dipping said dried plant materials into a hydrophilic blend of an acrylic base, water and a water dispersible adhesive or polymeric antitranspirant.

31. The method according to claim 30, wherein said sealing comprises topically coating said plant materials with a hydrophilic blend of polymer and pigment to seal and color said plant materials.

32. The method according to claim 31, wherein said polymer comprises a vinyl acetate/hydroxyethyl acrylate copolymer.

33. Natural plant materials treated according to the process of claim 31, wherein said materials contain ethylene glycol of specific gravity 1.025 to 1.10, sealed within said materials by a hydrophilic blend of polymer and pigment, said pigment coloring said plant materials.

34. The method according to claim 22, comprising the further steps of dipping said dried plant materials from step (d) into a hydrophilic polymer base and glue subcoating to seal and to mask the color of said materials, removing and drying said subcoated materials, and spray painting or dip-coating with one or more pigments blended with a water dispersible adhesive or polymeric medium to tint said materials.

35. Natural plant materials treated according to the process of claim 34, wherein said materials contain ethylene glycol of specific gravity 1.025 to 1.10, sealed within said materials by a hydrophillic polymer base and glue subcoating, and are spray painted with one or more pigments blended with a water dispersible adhesive or polymeric medium.

* * * * *